(12) United States Patent
Whitaker et al.

(10) Patent No.: US 7,381,521 B2
(45) Date of Patent: Jun. 3, 2008

(54) ANTI-PATHOGENIC COMPOSITION USEFUL IN BLOOD PRESERVATION

(75) Inventors: Barbee I. Whitaker, Millersville, MD (US); René-Guy Busnel, Bieures (FR)

(73) Assignee: Altachem Pharma Ltd., Alberta (CA)

( * ) Notice: Subject to any disclaimer, the term of this patent is extended or adjusted under 35 U.S.C. 154(b) by 0 days.

(21) Appl. No.: 10/496,261

(22) PCT Filed: Nov. 21, 2002

(86) PCT No.: PCT/CA02/01793

§ 371 (c)(1),
(2), (4) Date: Nov. 8, 2004

(87) PCT Pub. No.: WO03/043418

PCT Pub. Date: May 30, 2003

(65) Prior Publication Data

US 2005/0053516 A1    Mar. 10, 2005

Related U.S. Application Data

(60) Provisional application No. 60/331,806, filed on Nov. 21, 2001.

(51) Int. Cl.
*A01N 1/02* (2006.01)
*A61K 31/14* (2006.01)

(52) U.S. Cl. .......................... 435/2; 514/642

(58) Field of Classification Search ............... 514/642; 422/28
See application file for complete search history.

(56) References Cited

U.S. PATENT DOCUMENTS

| | | | | |
|---|---|---|---|---|
| 4,880,602 A | * | 11/1989 | Al-Sioufi | 422/28 |
| 4,961,923 A | * | 10/1990 | Heyde | 424/49 |
| 5,911,915 A | * | 6/1999 | Fonsny et al. | 424/405 |
| 5,942,217 A | * | 8/1999 | Woo et al. | 424/76.1 |
| 6,033,679 A | * | 3/2000 | Woo et al. | 424/401 |
| 6,080,706 A | * | 6/2000 | Blanvalet et al. | 510/108 |
| 6,106,738 A | * | 8/2000 | Woo et al. | 252/8.91 |
| 6,184,190 B1 | * | 2/2001 | D'Ambrogio et al. | 510/130 |
| 6,348,257 B1 | * | 2/2002 | Koike et al. | 428/206 |
| 6,372,701 B2 | * | 4/2002 | Aszman et al. | 510/191 |
| 6,488,948 B1 | * | 12/2002 | Danieli | 424/404 |
| 6,525,014 B1 | * | 2/2003 | Gorlin et al. | 510/439 |
| 6,649,580 B2 | * | 11/2003 | Aszman et al. | 510/180 |
| 6,667,287 B2 | * | 12/2003 | Aszman et al. | 510/191 |
| 6,689,223 B1 | * | 2/2004 | Meine et al. | 134/2 |
| 6,720,301 B2 | * | 4/2004 | Gorlin et al. | 510/439 |
| 6,730,648 B2 | * | 5/2004 | Gorlin et al. | 510/295 |

FOREIGN PATENT DOCUMENTS

| | | |
|---|---|---|
| EP | 0 338 515 | 10/1989 |
| EP | 0 379 269 | 7/1990 |
| EP | 0 457 656 | 11/1991 |
| EP | 0 555 116 A2 | 8/1993 |
| EP | 0 742 176 A1 | 11/1996 |
| WO | WO 88/09655 | * 12/1988 |

OTHER PUBLICATIONS

Burnof, T. Radosevich, M. Blood Reviews 2000, 14, 94-110.*
Reich, I., et al. "Tonicity, Osmoticity, Osmolality and Osmolarity" in Remington: The Science and Practice or Pharmacy, Nineteenth Edition, vol. I. Easton, PA: Mack, 1995. 613-627.*
Database WPI, XP 002230304, Derwent Publications Ltd., AN 2002-446750 (Relevant to JP 2001354505, Dec. 25, 2001, as listed in ISR), Abstract.
Database WPI, XP 002230305, Derwent Publications Ltd., AN 1990-264444 (Relevant to JP 2184609, Jul. 19, 1990, as listed in ISR), Abstract.

* cited by examiner

*Primary Examiner*—Mary E. Mosher
*Assistant Examiner*—Stuart W. Snyder
(74) *Attorney, Agent, or Firm*—Christine C. O'Day; Colleen J. McKiernan; Edwards Angell Palmer & Dodge LLP

(57) ABSTRACT

The present invention includes a method for reducing viral, bacterial, protozoan, fungal and other parasitic contamination from a biological solution. Biological solutions include, but are not limited to, solutions comprising blood, a blood component, cell culture or a component of a cell culture. In accordance with the present invention, there is provided, a method of inactivating a pathogen in blood or blood product in a container, comprising contacting at least one of said blood, blood product and container with a composition of the present invention. In accordance with the present invention, there is provided, a medical device comprising at least a surface treated with an anti-pathogenic composition of the present invention or containing at least an anti-pathogenic composition of present invention. In accordance with the present invention, there is provided, an anti-pathogenic composition for use in disinfecting fluids and biological tissues and surfaces contaminated with fluids and/or biological tissues, which comprises an anti-pathogenic amount of at least one quaternary ammonium compound in association with an acceptable carrier. A preferred anti-pathogenic composition of the present invention further comprises a bisguanidine compound. In accordance with the present invention, there is provided a method for inhibiting in vitro or ex vivo infection or replication of human immunodeficiency virus in a biological fluid, comprising treating said biological fluid with an effective inhibiting amount of a bis-guanidine compound or a derivative thereof, and at least one quaternary ammonium compound in combination with a pharmaceutically carrier, such as DMSO.

3 Claims, No Drawings

ANTI-PATHOGENIC COMPOSITION USEFUL IN BLOOD PRESERVATION

CROSS-REFERENCE TO RELATED APPLICATIONS

This application claims the prior benefit of U.S. provisional application Ser. No. 60/331,806, filed Nov. 21, 2001.

BACKGROUND OF THE INVENTION

1. Field of the Invention

The present invention relates to pathogenic compositions for use in blood and blood products, and blood containers, such as a blood donation bag. The present invention also relates generally to a method of processing and disinfecting human blood products. More particularly, this invention relates to a method of disinfecting whole blood, blood cells, plasma proteins, and plasma so that they may be used safely and effectively for diagnostic, therapeutic or research purposes. The present invention also relates to applications vis the blood circulatory system for controlling the pathological state produced by a pathogen, typically a viral, bacterial, protozoan, fungal or parasitic agent (at any stage of the life-cycle of the parasitic agent).

2. Description of Prior Art

The development of plastic blood collection bags has facilitated the separation of donated whole blood into its various components and analogous products, thereby making these different blood products (e.g., platelet concentrates) available as a transfusion product. With the passage of time and accumulation of research and clinical data, transfusion practices have changed greatly. One aspect of current practice is that whole blood is rarely administered; rather, patients needing red blood cells are given packed red cells, patients needing platelets are given platelet concentrate, and patients needing plasma are given plasma.

However, the increase in transfusing blood products finds a concomitant increase in the transmission of disease to the transfusion recipient. There is an existing and great need to assure a disease-free blood supply.

Blood products from human and animal donors are widely used for therapeutic, diagnostic and experimental purposes. A persistent problem associated with using blood products from human and animal donors is that these products are subject to contamination by blood-borne viruses and other micro-organisms such as bacteria. Of particular threat are viruses that appear to cause various forms of hepatitis, including the hepatitis B virus, the non-A, non-B hepatitis virus or viruses. Others of interest are cytomegalovirus and Epstein-Barr virus.

Viruses linked with the incurable and often fatal disease known as acquired immune deficiency syndrome (AIDS) are caused by a retrovirus or group of retroviruses (HIV, HIV-1, and HIV-2). The most common cause of AIDS is thought to be HIV-1.

The threat of hepatitis, AIDS, and bacterial transmission through transfusion and administration of blood products is not limited to blood cells but extends to the administration of plasma and plasma fractions such as Factor VIII concentrates, Factor IX concentrates, gamma globulin, and antithrombin III.

Disinfecting whole blood and blood products, including red blood cells, plasma, and plasma fractions with disinfectants strong enough to significantly inactivate viruses, bacteria and other organisms has generally been discounted because active agents strong enough to inactivate the pathogen typically damage cellular blood constituents or inactivate plasma and plasma protein factions. Additionally, the presence of any residual disinfectant in the blood product to be transfused could be hazardous to the recipient of the transfusion.

A typical component separation procedure used in the United States, the citrate-phosphate-dextrose-adenine (CPDA-1) system, utilizes a series of steps to separate donated blood into three components, each component having substantial therapeutic and monetary value. The procedure typically utilizes a blood collection bag which is integrally attached via flexible tubing to at least one, and preferably two or more, satellite bags. Using centrifugation, whole blood may be separated by differential sedimentation into such valuable blood components as plasma, packed red cells (PRC), platelets suspended in clear plasma (platelet-rich plasma, or PRP), platelet concentrate (PC), and cryoprecipitate (which may require extra processing).

Commonly used systems other than CPDA-1 include Adsol, Nutricell, and SAG-M. In these latter systems, the collection bag contains only anti-coagulant, and the nutrient solution may be pre-placed in a satellite bag. This nutrient solution is transferred into the PRC after the PRP has been separated from the PRC, thereby achieving a higher yield of plasma and longer storage life for the PRC. Improvements in current practices of viral marker screening and donor self-exclusion are continuously increasing the safety of the blood supply. However, despite these practices, a risk of transmission of pathogens with the transfusion of cellular components of blood remains since current screening tests do not screen for rarely occurring or as yet unknown transfusion transmissible pathogens (Dodd, R. Y. *New Engl. J. Med.* 327:419-421 (1992); Soland, E. M., et al. *J. Am. Med. Assoc.* 274:1368-1373 (1995); Schreiber, G. B., et al. *New Engl. J. Med.* 334:1685-1690 (1996)).

To combat the deficiencies associated with screening practices, the use of sterilization procedures of blood, red blood cell concentrates (RBCC), and other blood-derived components hold promise for eliminating pathogen transmission. In this connection, various approaches have been used to sterilize blood cells, the most efficacious so far use photochemical methods (Ben-Hur, E. and B. Horowitz *Photochem. Photobiol.* 62:383-388 (1995); Ben-Hur, E. and B. Horowitz *AIDS* 10:1183-1190 (1996)). The most promising photochemical methods employ the use of phthalocyanines (which are activated by light in the far red (660-700 nm)) for sterilization of RBCC (Horowitz, B., et al. *Transfusion* 31:102-108 (1991); Ben-Hur, E., et al. *J. Photochein. Photobiol. B:Biol.* 13:145-152 (1992)).

Pasteurization and other physical-chemical techniques have been used to remove or inactivate blood components, but most of these techniques have been limited to fresh plasma or fresh-frozen plasma. To date, these techniques are not suitable for treating cellular components of whole blood.

One disinfectant in use for blood products is beta-propiolactone. Beta-propiolactone, however, is a known carcinogen and hence potentially very dangerous. To the extent that significant residual amounts of this material may remain in the blood product which is actually transfused, the use of propiolactone represents a potential hazard.

There is described in U.S. Pat. No. 4,833,165 (issued on May 23, 1989, in the name of Allan Louderback) the use of as little as 0.1% formaldehyde and/or phenol to inactivate HTLV-III in blood. However, recently available data and information indicate that red blood cells treated with as little as 0.02% formaldehyde and 0.01% phenol are not viable and not suitable for transfusion.

Viral inactivation by stringent sterilization has not found acceptance since this method typically destroys erythrocytes, thrombocytes, and the labile plasma proteins, such as clotting factor VIII. Viable RBC's can be characterized by one or more of the following: capability of synthesizing ATP; cell morphology; $P_{50}$ values; filterability or deformability; oxyhemoglobin, methemoglobin and hemochrome values; MCV, MCH, and MCHC values; cell enzyme activity; and in vivo survival. Thus, if virally inactivated cells are damaged to the extent that the cells are not capable of metabolizing or synthesizing ATP, or the cell circulation is compromised, then their utility in transfusion medicine is compromised.

Viral inactivation by stringent steam sterilization is not acceptable for the above reasons. Dry heat sterilization, like wet steam, is harmful to blood cells and blood proteins at the levels needed to reduce viral infectivity. Use of stabilizing agents such as carbohydrates does not provide sufficient protection to the delicate blood cells and proteins from the general effects of exposure to high temperature and pressure.

Methods that are currently employed with purified plasma protein fractions, often followed by lyophilization of the protein preparation, include treatment with organic solvents and heat or extraction with detergents to disrupt the lipid coat of membrane enveloped viruses. Lyophilization (freeze-drying) alone has not proven sufficient to inactivate viruses, or to render blood proteins sufficiently stable to the effects of heat sterilization. The organic solvent or detergent method employed with purified blood proteins cannot be used with blood cells as these chemicals destroy the lipid membrane that surrounds the cells.

Another viral inactivation approach for plasma proteins first demonstrated in 1958 has involved the use of a chemical compound, beta-propiolactone, with ultraviolet (UV) irradiation. This method has not found acceptance in the United States due to concern over the toxicity of beta-propiolactone in the amounts used to achieve some demonstrable viral inactivation and also due to unacceptable levels of damage to the proteins caused by the chemical agents. Concern has also been raised over the explosive potential for beta-propiolactone as well. Attempts to inactivate viral decontaminants using photosensitizers and light have also been developed using some non-psoralen photosensitizers. The photosensitizers that have been employed are typically dyes. Examples include dihematoporphyrin ether (DHE), Merocyanine 540 (MC540) and methylene blue.

It would be highly desirable to be provided with anti-pathogenic compositions for use in blood and blood products, and blood containers, such as a blood donation bag.

It would be highly desirable to be provided with a method for processing and disinfecting human blood products.

It would be highly desirable to be provided with a method for disinfecting whole blood, blood cells, plasma proteins, and plasma so that they may be used safely and effectively for diagnostic, therapeutic or research purposes.

It would be highly desirable to be provided with a method vis the blood circulatory system for controlling the pathological state produced by a pathogen, typically a viral, bacterial, protozoan, fungal or parasitic agent.

SUMMARY OF THE INVENTION

One aim of the present invention is to provide an anti-pathogenic composition for use in blood and blood products, and blood containers, such as a blood donation bag.

Another aim of the present invention is to provide a method for processing and disinfecting human blood products.

Another aim of the present invention is to provide a method for disinfecting whole blood, blood cells, plasma proteins, and plasma so that they may be used safely and effectively for diagnostic, therapeutic or research purposes.

Another aim of the present invention is to provide a method vis the blood circulatory system for controlling the pathological state produced by a pathogen, typically a viral, bacterial, protozoan, fungal or parasitic agent.

In accordance with the present invention, there is provided, an anti-pathogenic composition for use in disinfecting fluids and biological tissues and surfaces contaminated with fluids and/or biological tissues, which comprises an anti-pathogenic amount of at least one quaternary ammonium compound in association with an acceptable carrier.

A preferred anti-pathogenic composition of the present invention further comprises a bisguanidine compound.

In a preferred anti-pathogenic composition of the present invention, the quaternary ammonium compound comprises a mixture of two or more quaternary ammonium compounds.

The fluids and biological tissues may be selected from the group consisting of water, water-based solutions, blood (i.e. whole blood) and blood products, skin and organs for transplantation.

The surfaces are selected from the group consisting of containers, filters, tubing, seals, clamps, transfer leg closures, medical devices, operating tables, and medical examination tables.

The containers may be biological fluid containers or water containers.

The container is a blood or blood product container, such as a blood donation bag or bottle.

The blood product may be selected from the group consisting of plasma, packed red cells, platelet-rich plasma, platelet concentrate and cryoprecipitate.

The composition may be in the form of a cream, ointment, lotion, gel, powder, detergent, soap, liquid, or solid.

In accordance with the present invention, there is provided, a method of inactivating a pathogen in blood or blood product in a container, comprising contacting at least one of said blood, blood product and container with a composition of the present invention.

In accordance with the present invention, there is provided, a medical device comprising at least a surface treated with an anti-pathogenic composition of the present invention or containing at least an anti-pathogenic composition of present invention.

The medical device may be a biological fluid container, such as blood donation bag or bottle, an in-line filter through which blood or blood product is passed prior to delivery to an individual, and an in-line filter through which blood or blood product is passed at the point of collection from an individual.

A preferred medical device of the present invention, further comprises a porous medium for dispensing said anti-pathogenic composition.

In accordance with the present invention, there is provided a method for treating in vitro or ex vivo biological fluid, comprising collecting a biological fluid in a container, and exposing the biological fluid to an anti-pathogenic composition of the present invention.

In accordance with the present invention, there is provided a method for inhibiting in vitro or ex vivo infection or replication of human immunodeficiency virus in a biological fluid, comprising treating said biological fluid with an effective inhibiting amount of a bis-guanidine compound or a derivative thereof, and at least one quaternary ammonium compound in combination with a pharmaceutically carrier, such as DMSO.

In accordance with the present invention, there is provided a method for in vitro or ex vivo disinfecting red blood cells, said process comprising the steps of:
a) contacting said red blood cells with a disinfecting composition for a period of time sufficient to inactivate pathogen present in said red blood cells, wherein said disinfecting composition consisting essentially of a disinfecting concentration of a bis-guanidine compound in association with a solution of an isotonic effective concentration of solute, whereby said disinfecting composition substantially isotonic with blood; and;
b) isolating said blood cells from said disinfecting composition.

In a preferred method of the present invention, the bis-guanidine compound is selected from the group consisting of quaternary ammonium compounds, and combinations thereof.

A preferred method of the present invention, further comprises removing the composition after inactivating the pathogen, or removing the composition after treating the biological fluid.

This invention relates to a system for processing blood donated for the purpose of therapeutic transfusion of blood components and, particularly, to improved methods and apparatuses for preparing pathogen-free or pathogen-inactivated blood or a blood component. This invention also relates to a biological fluid processing system for processing treated biological fluid into its various components.

The present invention is directed to compositions and methods for reducing the level of pathogens, e.g., infectious viruses and/or bacteria, that may be contained in a red blood cell composition. Specifically, the inventors of the present invention have found that exposing the red cell composition to a bisguanidine compound in or with a composition having one or more tension-active surfactants, such as quaternary ammonium compounds, inactivates the pathogen(s) sufficiently to allow the blood or blood product to be transfused, without damaging red blood cells or other blood constituents.

All references cited herein are incorporated by reference in their entirety.

DETAILED DESCRIPTION OF THE INVENTION

The present invention involves the effective and safe disinfection of whole blood and blood products. The invention has wide application to all blood products such as whole blood for transfusion, blood cells; blood plasma and blood plasma proteins. Since whole blood is rarely used, the present invention is more particularly directed to processes for disinfecting compositions containing red blood cells and/or blood plasma.

The present invention is a composition containing one or more tension-active surfactants as an active agent, such as a quaternary ammonium compound, suitable for use to disinfect blood or a blood product.

The present invention is also a method for treating blood or a blood product involving contacting the blood or blood product with a composition containing one or more compounds or active agents of the present invention, said compound being present in an amount sufficient to inactivate one or more pathogens in the blood, and allowing the compound to inactivate pathogen(s). The method may further include removing the compound from the blood or blood product.

The present invention may also be applied to viral inactivation of tissues and organs used for transplantation, and used in topical creams, ointments, lotions, gels, powders, liquids, solids, detergents or soaps for treatment of skin or epithelium disorders or for topical decontamination.

The present invention may also be used in the manufacture of viral vaccines for human or veterinary use, particularly to produce live, non-viable or attenuated viral vaccines.

The present invention includes a method for reducing viral, bacterial, protozoan, fungal and other parasitic contamination from a biological solution. Biological solutions include, but are not limited to, solutions comprising blood, a blood component, cell culture or a component of a cell culture. The method comprises mixing the composition in a liquid state with a composition of the present invention capable of binding to the viral, bacterial protozoan, fungal or parasitic contamination.

The present invention is also a method for reducing viral, bacterial, protozoan, fungal and other parasitic contamination from medical devices, such as those employed by a doctor, nurse, medical technician such as one who collects blood or blood products, or dentist involving contacting the medical device with a composition containing one or more compounds or active agents of the present invention, said compound being present in an amount sufficient to inactivate one or more pathogens in or on the medical device, and allowing the compound to inactivate pathogen(s). The method may further include removing the compound from the medical device.

The term "medical device" is intended to mean any tool employed in the checking, cleaning, collection of fluid from or medical intervention of an animal or human body. Such tools include, without limitation, surgical instruments such as, but not limited to, probes, scalpels, clamps, forceps, needles, suction devices for removing saliva or blood including all nozzles, seals, tubing, filters, containers and reservoirs therein, endoscopes, optical fibers, transducers, wire, surgical loops, and in-line and out-line tubing and filters through which blood or blood product is passed prior to delivery to an individual and/or at the point of collection from an individual.

The present invention is also a method for reducing viral, bacterial, protozoan, fungal and other parasitic contamination from water or water containers such as found in swimming pools, hot-tubs, Jacuzzis, baths, and whirlpool baths, air-conditioners and humidifiers, involving contacting the water or water container with a composition containing one or more compounds or active agents of the present invention, said compound being present in an amount sufficient to inactivate one or more pathogens in the water or on the water container, and allowing the compound to inactivate pathogen(s). The method may further include removing the compound from the water or water container. Such water and water containers can be those found in the home, a hotel, spa or resort, office, or storage building.

The present invention also includes one or more compositions specific for a particular blood type.

The present invention is also a blood container, or the like, e.g., a blood or blood product transfusion bag, containing one or more compounds of the present invention.

In the most preferred embodiments of the invention, a composition containing quaternary ammonium compounds as the active agent, alone or in a mixture, are mixed with blood or a blood product, and used to disinfect the blood. The composition is effective for treating blood, blood products, biological tissues, and other biological fluids. The active agent is useful against a wide variety of pathogens, including but not limited to viruses, bacteria, protozoa, parasites, fungi, and other pathogens. A most preferred composition includes one or more quaternary ammonium compounds, and, optionally, a bis-guanidine compound.

In accordance with the preferred method for disinfecting blood products, a method is provided in which viruses and bacteria including the HIV viruses, in whole blood and blood products are inactivated. Once disinfected the blood and blood products may be used for therapeutic or diagnostic purposes in a safe and effective manner. The invention is based upon the unexpected discovery that the compounds do not lyse red blood cells or cause harm to blood products, and are therefore useful as disinfectants to remove pathogens from the blood or blood product. Moreover, disinfectant compositions containing these compounds which are not isotonic with respect to blood, and which until now have not been considered for use with blood products, can be used to disinfect plasma and plasma proteins without denaturing the protein or otherwise causing a substantial loss in physiological activity.

In accordance with the present invention, methods for disinfecting whole blood or blood products are provided which include the steps of providing a disinfectant composition of a disinfecting concentration of an active agent or compound and a diluent, and then mixing whole blood or blood product with the disinfecting composition for a length of time sufficient to inactivate any pathogen present in the blood or blood product. The mixing step may be performed by mixing the blood with the constituents of the composition separately, mixing directly with a complete composition, or by timing the additional of one or more constituents of the composition. After the blood or blood product is disinfected, the active agent or compound may be optionally separated from the disinfecting composition, providing blood or blood product which is safe and effective for therapeutic or diagnostic use.

The term "pharmaceutically acceptable carrier" is intended to mean any carrier which may be used to solubilize and/or dilute said quaternary ammonium compound in an efficient anti-pathogenic concentration, including without limitation, saline, buffer, DMSO and dextrose.

The term "bis-guanidine compounds" and "quaternary ammonium compounds" is intended to mean all quaternary ammonium compounds and their derivatives, including without limitation, didecyl dimethylammonium chloride, all diaminopropyl laurylamine compounds, nonoxynol-9 compounds, bis-guanidine compounds and their derivatives. The term "compounds" shall also include any of the chemicals noted above, alone or associated with another chemical or substance, e.g., in mixing solutions, including but not limited to DMSO. The preferred active agents are alkyl trimethyl quaternary ammonium chlorhexidrine (and their halogens); dialkyl dimethyl benzyl quaternary ammonium chlorhexidrine. Exemplary quaternary compounds are described in Marchisio, et al., *J. Biomater. Sci. Polymer Edn.* 6:533-539 (1994), and Cadwallader, et al., *J. Pharm. Sci.*, 7:1010-1012 (1965), both incorporated by reference in their entirety.

The composition containing the active agent may also include one or more additional compounds, as desired. These compounds may include DMSO, or other agent that changes the polarity of the cell surface; one or more amino acids; a diluent; one or more chlorides, such as silver chloride; and/or EDTA.

As described below, the above identified compounds will effectively disinfect blood and blood products without substantial loss of physiological activity. It is also contemplated as being within the teachings of the present invention to disinfect blood or blood products with oxidizing compounds having sufficient oxidizing properties to inactivate pathogens, such as viruses, bacteria, protozoa, fungi, and parasitic agents.

The term "fluid" is intended to mean water, water-based solutions and biological fluid.

The term "biological tissue" is intended to mean skin and organs used for transplantation.

As used herein, biological fluid refers to any fluid that may be transfused directly into a patient or into the circulatory system of the patient. Typical biological fluids include but are not limited to: whole blood; anti-coagulated whole blood (AWB); packed red cells obtained from AWB; platelet-rich plasma (PRP) obtained from AWB; platelet concentrate (PC) obtained from AWB or PRP; plasma obtained from AWB or PRP; red cells separated from plasma and resuspended in physiological fluid; and platelets separated from plasma and resuspended in physiological fluid. Blood product or biological fluid also includes any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelet concentrate (PC), platelet-rich plasma (PRP, platelet-free plasma, platelet-poor plasma, plasma, or packed red cells (PRC); analogous blood products derived from blood or a blood component or derived from bone marrow. The biological fluid may include leucocytes, or may be treated to remove leucocytes. As used herein, blood product or biological fluid refers to the components described above, and to similar blood products or biological fluids obtained by other means and with similar properties. In accordance with the invention, each of these blood products or biological fluids may be processed in the manner described herein.

As used herein, pathogen refers to one or more microorganisms or the like that cause infection. Exemplary pathogens include, but are not limited to a virus, bacteria, parasite, protozoa or fungus. An exemplary virus includes, but is not limited to Herpes simplex virus, HIV, hepatitis, hepatitis A, hepatitis B, hepatitis C, Respiratory syncycial virus, blue tongue virus, and bovine diarrhea virus. Virus also includes Cytomegalovirus, Epstein-Barr virus, Herpes Simplex type I and II viruses, and other viruses that circulate freely in the blood, as well as cell-associated viruses. An exemplary bacteria includes, but is not limited to, *Heliobacter pylori, E. coli, Pseudomotias strains*, including *aeruginosa, Staplhylococcus, Proteus vulgaris*, and *Candida albicans*. An exemplary fungus includes, but is not limited to. *Aspergillus*. Typical parasites include, but are not limited to: *Ameoba, Plasmodiunm, Leishmania, Mycosus profundus, Trypanosoma, Spirochete*, and *Arbovius*.

In a preferred embodiment of the invention, the pathogen being treated is one that is suited to being inactivated while in blood or a blood product. Reducing the level of infectious pathogen, or similar words, refers to destroying and/or inactivating all or substantially all of the infectious pathogen. In a preferred embodiment of the invention, reducing the level of infectious pathogen refers to destroying or inactivating the pathogen sufficiently so that the blood or blood product may be transfused or otherwise used.

In accordance with the present invention, suitable diluents include any of a number of compounds used in the preparation of isotonic solutions. Exemplary solutes include but are not limited to sugars such as dextrose and glucose, polysaccharides such as dextran, albumin, and salts of alkali earth metals including sodium chloride, potassium chloride, and potassium bromide. Combinations of solutes known for their utility in storing physiological cells and tissue are also suitable and include such combinations as citrate-phosphate-dextrose, citrate-phosphate-dextrose-adenine, and saline-mannitol-dextrose-adenine. As described in greater detail below, the presence of at least one solute in the diluent in the form of a sugar is preferred because sugar contributes to the reduction of any methemoglobin, oxidized hemoglobulin, formed during the disinfecting process.

Diluents having utility in the practice of the present invention for their isotonic characteristics can be combined. Combining diluents is particularly suitable when disinfecting red blood cells because commercial collective units of red blood cells are frequently stored in isotonic solutions containing anti-coagulant, such as ACID (acid-citrate-dextrose), CPD (citrate-phosphate-dextrose), CPD-A (CPD-adenine). Thus, when disinfecting collective units of red blood cells stored in isotonic solutions of anti-coagulant, the disinfectant composition may be prepared in a different isotonic diluent, e.g., normal saline, and combined with the anti-coagulant solution.

Further in accordance the present invention, processes for disinfecting plasma or plasma products, such as plasma protein fractions, optionally utilize disinfecting compositions having no solute and in which the diluent is sterile water, water, distilled water or sterile and distilled water. Because plasma and plasma products do not contain tissue or other forms of cellular material, there is no compelling need to have an isotonic medium for maintaining cellular osmotic pressure.

Mixing a disinfectant composition with blood or blood products can be performed by simply combining the blood or blood product and disinfectant composition in a suitable container with light agitation to assure sufficient interaction between the blood and disinfectant composition. Suitable containers include but are not limited to blood collection bags and blood storage apparatus. It is preferable, however, to utilize automated cell washing equipment known in the art and available from a variety of sources including Cobe.

In accordance with the present invention disinfecting effective concentrations of quaternary ammonium compounds, preferably quaternary ammonium associated with bis-guanidine, and sufficient periods of time for disinfecting blood and blood products are primarily dependent upon the choice of compound. It can also be appreciated that useful concentrations of each constituent of the composition and periods of time for disinfecting are interdependent. Thus, compound concentrations can be varied and a relatively small concentration of one or more active agents can be a disinfecting effective concentration when mixed with blood or blood products for longer lengths of time. Conversely, when relatively larger concentrations of an agent are utilized in disinfectant compositions, the period of time sufficient to disinfect blood or blood products is less.

An exemplary process for disinfecting blood or a blood product may include first mixing the blood with DMSO, agitating, adding an amount of a surfactant active agent such as quaternary ammonium or bis-guanidine in a dose so that the active agent does not precipitate, and agitating. The process may optionally include a further step of removing the active agent from the blood composition.

The invention also involves a method for collecting and processing blood comprising collecting blood or a blood product in a container; optionally removing or separating a blood product, e.g., plasma, and contacting the blood or blood product with a composition containing an amount of active agent sufficient to inactivate a pathogen in the blood or blood product.

The containers which are used in the biological fluid processing assembly may be constructed of any material compatible with a biological fluid, such as whole blood or a blood component, and capable of withstanding a centrifugation and sterilization environment. A wide variety of these containers is already known in the art. For example, blood collection and satellite bags are typically made from plasticized polyvinyl chloride, e.g. PVC plasticized with dioctylphthalate, diethylhexylphthalate, or trioctyltrimellitate. The bags may also be formed from polyolefin, polyurethane, polyester, and polycarbonate.

As used herein, the tubing may be any conduit or means which provides fluid communication between the containers, and is typically made from the same flexible material as is used for the containers, preferably plasticized PVC. The tubing may extend into the interior of the container, and may be used as a siphon, for example. There may be a number of tubes providing fluid communication to any individual container, and the tubes may be oriented in a number of ways. For example, there may be at least two tubes oriented at the top of the collection bag, or at the bottom of the bag, or a tube at each end of the bag.

A seal, valve, clamp, transfer leg closure, or the like is typically located in or on the tubing. It is intended that the present invention is not limited by the type of material used to construct the containers or the conduit which connects the containers.

A number of additional containers may be in communication with the biological fluid processing system, and can be utilized to define different flow paths. For example, an additional satellite bag containing physiological solution may be placed in communication with the biological fluid processing system.

In accordance with the invention, the biological fluid collection and processing assembly should be able to withstand rigorous sterilization and centrifugation environments, typically consisting of radiation sterilization (at about 2.5 megarads), and/or autoclaving (at about 110° C. to about 120° C. for about 15 to 60 minutes), and/or centrifugation (typically about 2500 to 3500 G for about 5 to 15 minutes; however, depending on which biological fluid component is intended to have maximum recovery, the centrifugation may be about 5000 G for about 10 to 20 minutes).

The present invention will be more readily understood by referring to the following examples which are given to illustrate the invention rather than to limit its scope.

EXAMPLE 1

Methodology of a Test for Inhibition of HIV-1 Viral Activity

One can screen the bis-guanidine for inhibition of HIV using various experimental techniques. One technique involves the inhibition of viral replication in human peripheral blood mononuclear (PBM) cells. The amount of virus produced is determined by measuring the quantity of virus-coded reverse transcriptase (an enzyme found in retroviruses) which is present in the culture medium. Another technique involves measuring inhibition of purified reverse transcriptase activity in a cell free system. Examples of methods for screening which are known to those skilled in the art are described in more detail as follows.

Methodology for Testing Antiviral Drugs for Inhibition or Replication of HIV-1 in Human Peripheral Blood Mononuclear (EBM)

Cells from HIV-1 and B virus seronegative donors are isolated by Ficoll-Hypaque discontinuous gradient centrifugation at 1,000 times/g for 30 minutes, washed twice in PBS and pelleted at 300 times/g for 10 minutes. Before infection, the cells are stimulated by phytohemagglutinin (PHA) at a concentration of 16.7 µg/ml for three days in RPMI 1640 medium supplemented with 15% heat-inactivated fetal calf serum, 1.5 mM L-glutamine, penicillin (100 U/ml), streptomycin (100 µg/ml), and 4 mM sodium bicarbonate buffer.

HIV-1 (strain LAV-1) is obtained from the Center for Disease Control, Atlanta, and propagated in PHA-stimulated human PBM cells using RPMI 1640 medium as above without PHA and supplemented with 7% interleukin-2 (Advanced Biotechnologies, Silver Spring, Md.), 7 µg/ml DEAE-dextran (Pharmacia, Uppsala, Sweden), and 370 U/ml anti-human leukocyte (alpha) interferon (ICN, Lisle, Ill.). Virus is obtained from cell-free culture supernatant and stored in aliquots at −70° C. until used.

Medium Used for Cellular Culture

The study of cytotoxicity having been conducted on a line T, the culture medium corresponds to RPMI 1640 supplemented by 10% fetal calf serum (BIO-LAB), 1% glutamine (GIBCO), 1% antibiotics (PSN, GIBCO).

For the study of the residual infectious strength after treatment of viral preparations, the culture medium of normal human lymphocytes T (complete medium) corresponds to the above medium to which are added 10% interleukin II, polybrene (2 mg/ml) and human anti-interferon serum (1.2500 (M. A. Rey et al), Biochem. Biophys. Res. Corn., 1984, 121 126-133).

Cells

The cytotoxicity is studied on a CEM cell clone, line of immature T lymphocytes.

Infectivity is studied on T lymphocytes obtained from peripheral blood of a healthy human donor and separated on a Ficoll gradient.

The lymphocytes are stimulated for 3 days by phytohaemaglutinin P (PHA P) diluted to 1/500 and cultivated in a complete medium. The blastic cells T are infected by the virus, treated or not, in order to show up residual infectious strength.

HIV-1 Virus

The viruses obtained from a supernatant culture of an HIV-1 infected CEM line. This T lymphoblastoid line infected by HIV-1 is used for viral production.

The titer of the supernatant substances used is evaluated after quantitative analysis of the reverse transcriptase activity (ATI) of the virus.

In the following tests, a supernatant substance was used, the ATI of which was $1.8 \times 10^6$ cpm/ml.

Methods

Study of the Cytotoxicity of Compounds for T Cells

Cells: cellular suspension of the CEM clone with $1 \times 10^6$ cells/ml.

Products: various dilutions in the medium RPMI 1640 are prepared from the compounds which was a QACs, Bardac22®.

On a cellular culture plate with 24 wells, 0.5 ml of each of the dilutions are incubated with 0.5 ml of cellular suspension of the CEM clone ($5 \times 10^5$ cells) in an incubator at 37° C.

Cellular growth is evaluated after counting the cellular suspensions with Tryptan Blue® in comparison with a control comprising untreated cells.

Action of the Bardac, Alone or in Association on the Infectious Capacity of the HIV-1 Virus for Normal Human Lymphocytes T (MLC)

Preparation of the viral solution: several tubes containing 1 ml viral supernatant, ATI $1.8 \times 10^6$ cmp/ml are, concentrated by ultracentrifugation. The resulting virus residues are taken up either by each of the different dilutions of QACs produced in sterile bidistilled water or by water (untreated control virus).

Treatment of viral preparations: the concentrated viral preparations are all treated according to the following procedure:

Treated virus samples: the virus residues concentrated by ultracentrifugation are resuspended in 100, µl of each of the concentrations in terms of products (QACs) studied and incubated for 10 minutes.

Control viral sample: untreated control virus: the product is replaced by 100 µl of sterile bidistilled water.

Following this 10 minute incubation time, the virus present in each sample is rinsed and then reconcentrated by addition of 12 ml of RPMI 1640 medium and ultracentrifugation. The virus residues are then taken up in 1 ml of complete medium and used for infecting normal human T lymphocytes.

Measurement of the infectivity of the samples: $4 \times 10^6$ normal human T lymphocytes are infected with each of the treated viral preparations or controls mentioned hereinabove. Infection of the T cells is carried out according to a previously described method (F. Barre Sinoussi et al. Science, 1983, 220:868-871): to sum up, $4 \times 10^6$ cells in suspension in 1 ml of complete medium are incubated with 1 ml of each of the treated vial preparations or controls for 1 hour at 37° C.

After two washings using several millilitres of culture medium, the cellular suspensions are adjusted to the concentration of $1 \times 10^6$ cells per ml. The day of the infection is regarded as day 0.

Control cells: $4 \times 10^6$ T lymphocytes are cultivated and are passed every 3 or 4 days under the same conditions as all the other samples.

This control corresponds to the negative control from viral production during the course of handling.

Viral production during the course of time is determined by measuring the reverse transcriptase activity present in the culture supernatants using the procedure described below.

Measurement of the Reverse Transcriptase Activity of the Control Viral Preparations and the Viral Samples Treated by the Products This quantitative analysis makes it possible to evaluate the presence of noninactivated residual virus in the staring sample. It is carried out on a basis of 1 ml of culture supernatant taken every 2 or 3 days and ultracentrifuged.

The enzymatic activities are measured in 50 µl of a reaction mixture containing 50 mM Tris pH 7.8, 20 mM MgCl$_2$, 20 mM KCl, 2 mM dithiotreitol, 0.25 OD/ml, oligo dT, 0.25 OD/ml poly rA, 0.1% Triton×100 and 2.5 μCi 3H DTTP.

After incubation for 1 hour at 37° C., the reaction is stopped by the addition of 10 μl of 0.2 M EDTA and the samples are deposited on DE81 membranes.

After several washings using 5% Na$_2$HPO$_4$, then by distilled water, the membranes are dried and the radioactivity measured by means of a p scintillation counter (PACKARD).

Results

Table I shows the effect of a treatment of viral samples by various products on the infectivity of the HIV-1 virus.

TABLE II

| Mixtures tested | | | | |
|---|---|---|---|---|
| Bardac ® (%) | + | CHG* (%) | Bardac ® alone | CHG alone |
| 0.2 | – | 0.25 | 0.2 | 0.25 |
| 0.1 | – | 0.1 | 0.1 | 0.1 |
| 0.04 | – | 0.05 | 0.04 | 0.05 |
| 0.2 | – | 0.05 | | |
| 0.04 | – | 0.25 | | |

*CHG corresponds to an abbreviation for chlorohexidine digluconate

TABLE I

| Quantitative Analysis Of ATI in the Supernatant Substances On Infected Cultures (cpm/ml) | | | | | | | | | |
|---|---|---|---|---|---|---|---|---|---|
| | J3 | J6 | J10 | J13 | J17 | J20 | J23 | J27 | J30 |
| Bardac ® (%) | | | | | | | | | |
| 0.01 | 334 | 222 | 1768 | 1592 | 190 | 390 | 1328 | 780 | 1000 |
| 0.006 | 320 | 326 | 204 | 248 | 364 | 180 | 328 | 588 | 196 |
| 0.004 | 346 | 298 | 160 | 170 | 350 | 218 | 444 | 244 | 264 |
| 0.002 | 464 | 2472 | 16066 | 24902 | 77754 | 75554 | 101394 | 80560 | 64692 |
| 0.0004 | 702 | 18136 | 117326 | 74214 | 50674 | 22478 | 13806 | 7800 | 4426 |
| Chlorhexidine (%) | | | | | | | | | |
| 0.01 | 262 | 274 | 200 | 250 | 230 | 272 | 456 | 420 | 276 |
| 0.005 | 360 | 374 | 580 | 742 | 1902 | 1126 | 1226 | 528 | 720 |
| 0.002 | 252 | 352 | 1304 | 1752 | 4288 | 6138 | 4614 | 1616 | 4528 |
| Bardac ® + Chlorhexidine (%) | | | | | | | | | |
| 0.006 + 0.01 | 336 | 202 | 116 | 226 | 280 | 236 | 342 | 510 | 240 |
| 0.006 + 0.005 | 326 | 196 | 210 | 384 | 274 | 166 | 280 | 406 | 304 |
| 0.006 + 0.002 | 286 | 240 | 196 | 282 | 192 | 274 | 376 | 478 | 330 |
| 0.004 + 0.01 | 302 | 326 | 210 | 222 | 240 | 350 | 366 | 278 | 248 |
| 0.004 + 0.005 | 298 | 288 | 206 | 344 | 170 | 346 | 288 | 456 | 282 |
| 0.004 + 0.002 | 228 | 268 | 208 | 232 | 1200 | 274 | 254 | 422 | 250 |
| 0.002 + 0.01 | 666 | 262 | 222 | 200 | 244 | 394 | 650 | 322 | 280 |
| 0.002 + 0.005 | 364 | 246 | 314 | 308 | 4386 | 308 | 268 | 446 | 254 |
| 0.002 + 0.002 | 998 | 222 | 666 | 908 | 748 | 1206 | 1110 | 370 | 336 |
| 0.0004 + 0.01 | 2163 | 234 | 186 | 226 | 204 | 250 | 344 | 352 | 226 |
| 0.0004 + 0.005 | 438 | 246 | 824 | 1142 | 2340 | 2190 | 2120 | 1094 | 1466 |
| 0.0004 + 0.002 | 576 | 3362 | 21734 | 36246 | 39364 | 40126 | 18480 | 6530 | 10476 |
| T1 | 1516 | 3120 | 24822 | 52912 | 49884 | 30540 | 21800 | 4500 | 3464 |
| T2 | 342 | 4688 | 61384 | 64284 | 69172 | 15366 | 12364 | 3500 | 3790 |
| T3 | 1594 | 45068 | 75046 | 56928 | 12872 | 8932 | 5468 | 1050 | 1746 |
| T4 | 232 | 220 | 218 | 202 | 190 | 268 | 394 | 244 | 308 |

T1: control virus treated by 100 μl of bidistilled water
T2: control virus treated by 100 μl bidistilled water
T3: control virus, verification
T4: control cells, not infected Table I clearly shows the synergy of action of the association of Bardac®/chlorohexidine digluconate at low concentration (concentration 0.002+0.002) which shows the absence of virus on the thirtieth day; indeed, at the same concentrations, the two products used by themselves are not virocidal.

EXAMPLE 2

Virocidal Action of Compositions According to the Invention on HBV Viruses

Action on In Vitro Degradation of the Antigen of Hepatitis B Virus (AgHBs) of the Hepatitis B Virus: Virocide+Human Serum Taken from a Patient with Hepatitis B (1/1000th)

TABLE III

| Results | |
|---|---|
| Virocide tested | Residual AgHBs (ratio) |
| Bardac ® 0.2% | 1.35 |
| Bardac ® 0.1% – CHG 0.1% | 2.18 |
| Bardac ® 0.2% – CHG 0.05% | 3.07 |
| Bardac ® 0.2% – CHG 0.25% | 3.23 |

The mixture comprising 0.1% Bardac® and 0.1% CHG displays interesting activity even though the dose is reduced by 50% compared with 0.2% Bardac® by itself.

General Conclusion on the Various Mixtures Tested

Only the antigen of the residual virus of hepatitis B makes it possible to discriminate among the Bardac®-CHG mixtures tested.

It appears that 0.02% Bardac® in association with 0.025% of CHG is as effective as Bardac® at 0.1%. This reduction by a factor of 5 is significant and important, particularly in the application of a composition according to the invention in conjunction with an elastomeric material, Bardac® being particularly toxic to the elastomer.

EXAMPLE 3

Virocidal Action of Compositions According to the Invention Against Herpes Simplex Virus (HSV)

Tests In Vitro

Tests Conducted

The viral strain: This is a strain of the herpes virus Hominis type 1, strain Bey (HSV1), it is kept alive on human fibroblastic cells or on KB cells and has undergone a number of important changes on one or other type of cell.

A viral batch is used which is frozen at −80° C. after obtaining a cytopathic effect which reached at least 80% of the cells, without prior centrifugal treatment, which would have removed most of the cellular debris from the inoculum; indeed, it appears that the infectivity of the virus disappears very rapidly when it is extra-cellular and in consequence one is closer to the reality of in vivo infection when one uses a viral batch in which the virions can still be found in cellular debris.

This batch was titrated after distribution into aliquot parts of 0.5 ml, maintained at −80° C., on human fibroblastic cells:
  by dilution of 1 in 10 and inoculations of 8 culture tubes by dilution: $10^6$ ml; and
  by inoculation of cultures in Petri dishes (35 mm) and the addition of anti-HSV1 serum into the supernatant in order to neutralize the varions which might be released into the liquid medium, so making it possible to count zones: 100 to 150 units forming zones per dish inoculated with 0.5 ml of a viral solution diluted to $10^{-4}$.

Cytotoxicity checks are conducted on the products for cellular cultures used in the tests, that is to say the human fibroblastic cells.

The cells are cultivated on a Dulbecco medium enriched with 10% fetal calf serum; at the moment of their use, the cells are washed and the same culture medium is used but without calf serum.

For each product tested or each composition, 10 tubes of cellular culture were used and after inoculation of the product, the tubes were kept under observation for 3 days.

Action Observed with the Various Products by Themselves

Each product was, in succession, used pure and at dilutions of $10^{-1}$, $10^{-2}$, $10^{-3}$ and added to culture tubes containing 1 ml of nutrient medium in a volume of 0.1 ml.

Results

Bardac® 0.04% solution: not toxic at a dilution of $10^{-3}$ chlorohexidine digluconate, 0.05% solution: no toxicity.

Immediate Virocidal Action Observed

Measurement of activity: 0.2 ml viral suspension is mixed with 0.2 ml of one of the diluted solutions of the test compound. There is then an immediate dilution of 0.2 ml of mixture at the rate of $10^{-4}$ which stops the activity of the product. This dilution of mixture is deposited in a volume of 1 ml on a layer of vero cells cultivated in a Petri dish 6 cm in diameter.

After 1 hour of adsorption, the supernatant liquid is drawn off and replaced by 5 ml of culture medium with no animal serum but to which has been added 1% of a type 1 polyclonal rabbit serum, anti-herpes type.

This does not interfere with multiplication of the inter-cellular virus but neutralizes the particles which pass into the liquid phase during destruction of the infected cells; at the end of 4 to 5 days, it is possible with the naked eye to observe zones of cellular lysis which extend like a spot of oil, each theoretically corresponding to the multiplication of "a zone-forming unit" (UFP) present in the viral dilution which was deposited on the culture. A zone-forming unit may be roughly evaluated as equivalent to an infecting particle or even a virion.

TABLE IV

Number of zone-forming units per milliliter of virus diluted to $10^{-4}$ (titration carried out on three culture dishes) on day 4

| Bardac ® 0.02% | Bardac ® 0.02% + digluconate 0.025% | Control virus at $10^{-4}$, $10^{-5}$, $10^{-6}$ |
|---|---|---|
| 30/125/45 | 17/26/16 | 1/223/51 |

| Bardac ® | Bardac ® + digluconate 0.05% | Control virus at $10^{-6}$ |
|---|---|---|
| 26/17/20 | 9/6/8 | 14/32/30 |

Period of Appearance of Activity 0.2 ml of the non-diluted viral suspension are mixed with 0.2 ml of each of two following mixtures:
  0.04% Bardac®+0.05% CHG (digluconate)
  0.02% Bardac®+0.025% CHG After incubation for 1, 5 and 15 minutes a drop of mixture is inoculated into 5 culture tubes and kept under observation for 5 days.

As a control, the diluted virus is sown in the same way into culture medium instead of the mixtures.

TABLE V

Results observed on day 2 on 5 tubes for the two mixtures mentioned

| Virus + mixture | Cytopathic effect (on day 2) | Control virus |
|---|---|---|
| 2/5 | 1 minute | 5/5 |
| 0/5 | 5 minutes | 5/5 |
| 0/5 | 15 minutes | 5/5 |

Tests in vivo

Tests conducted on Nude mice, either injected intramuscularly with a needle steeped in a viral suspension or injected after passage of the infected needle (that is to say steeped in a viral suspension) through microcapsules such as are described hereinafter (Example 8, sample 1) covered with latex, shown at the passage of the needles through the microcapsules permits of a quite significant and instant level of the infection of the animals.

The operative procedure is similar to that in Example 8 except for the culture media which must be suitable for the herpes virus.

EXAMPLE 4

Bactericidal Action of Compositions

Test I

Materials

Micro-organisms tested
reference strains
*Pseudomonas aeruginosa* CIP A22
*Escherichia coli* CIP 54127
*Staphylococcus aureus* CIP 5314 Oxford strain
hospital strains:
*Pseudomonas aeruginosa*
*Escherichia coli*
*Staphylococcus aureus*
*Proteus vulgaris*
*Candida albicans*
Millipore membranes: HAE P047SO (0.45 μm)
Mueller Hinton 2 gelose: 4 3301 (Biomerieux)
sterile and apyrogenic distilled water (biosedra)

Procedure

Maintenance of the Strains

Each strain of bacteria underwent three sub-culturings on Mueller Hinton geloses at 24-hour intervals prior to use.

Preparation of the Bacterial Inocula
initial bacterial suspension: A
Prepared on the basis of a bacterial isolation, it must correspond to an opacity equivalent to point 1 on the McFarland scale. It will be used for the final tests.
suspension used for controls and preliminary tests: B
It is prepared by successive dilutions of suspension A down to $10^{-6}$.

Control Group 1 ml of suspension B is sown "en masse" with a Mueller Hinton gelose Control Filtration Counts 1 ml of suspension B is filtered over a millipore membrane and washed with 50 ml distilled water.
Enumeration of colonies after 24 hours at 37° C.

Preliminary Tests

For each of the four antiseptic mixtures and for each bacterial strain, the following test was conducted:
filtration of 1 ml of antiseptic mixture
washing (twice in 50 ml of distilled water)
filtration of 1 ml of suspension B
rinsing using 50 ml of distilled water
enumeration of colonies on the membrane after 24 hours at 37° C.

Final Tests

Each antiseptic mixture at double concentration is placed for 1, 5 and 10 minutes in contact with 1 ml of suspension A and then filtered.
After the washing stages defined by the preliminary test, the membranes are placed at 37° C. for 25 hours.

Interpretation of the Results

In the procedure adopted a mixture intended to be antiseptic is regarded as bactericidal if, after a specific contact time, it reduces the bacterial inoculum by at least 5 logarithms.

This effect is visualized by counting, on the final test membranes, a number of colonies compared with that observed in the preliminary tests corresponding to the same strain and the same mixture.

Results

TABLE VI

Efficacy of Composition at t = 1 min

| Strain | Mixture No. 1 Bardac ® 4% | Mixture No. 2 Bardac ® 0.04 g/100 ml Digluconate 0.05 g/100 ml |
|---|---|---|
| *S. aureus* CIP 53154 | E | E |
| *E. coli* CIP 54127 | E | E |
| *P. aeruginosa* CPI A22 | E | E |
| *S. aureus* | E | E |
| *E. coli* | E | E |
| *P. aeruginosa* | NE | E |
| *P. vulgaris* | NE | NE |
| *C. albicans* | E | E |

E or NE (Effective or Not Effective)

TABLE VII

Efficacy of Composition at t = 5 min

| Strain | Mixture No. 1 Bardac ® 4% | Mixture No. 2 Bardac ® 0.04 g/100 ml Digluconate 0.05 g/100 ml |
|---|---|---|
| *S. aureus* CIP 53154 | E | E |
| *E. coli* CIP 54127 | E | E |
| *P. aeruginosa* CPI A22 | E | E |
| *S. aureus* | E | E |
| *E. coli* | E | E |
| *P. aeruginosa* | NE | E |
| *P. vulgaris* | NE | NE |
| *C. albicans* | E | E |

E or NE (Effective or Not Effective)

TABLE VIII

Efficacy of Composition at t = 10 min

| Strain | Mixture No. 1 Bardac ® 4% | Mixture No. 2 Bardac ® 0.04 g/100 ml Digluconate 0.05 g/100 ml |
|---|---|---|
| *S. aureus* CIP 53154 | E | E |
| *E. coli* CIP 54127 | E | E |
| *P. aeruginosa* CPI A22 | E | E |
| *S. aureus* | E | E |
| *E. coli* | E | E |
| *P. aeruginosa* | E | E |
| *P. vulgaris* | E | E |
| *C. albicans* | E | E |

E or NE (Effective or Not Effective)

Conclusion

After 1 minute of contact, no mixture was effective on all the strains studied. Mixture No. 2 is however the most efficient because only one strain of *Proteus vulgaris* appears to be insensitive.

After 5 minutes of contact, mixture No. 2 could be considered as effective were it not for the same strain of *Proteus vulgaris* which resists the product even after 5 mins.

After 10 minutes of contact, mixtures Nos. 1 and 2 give satisfactory results over all the strains studied.

Test 2

Another test was carried out a basis of the following solutions
  100 ml of a 0.1% solution of chlorohexidine digluconate (pH 6); and
  100 ml of a 0.1% solution of Bardac22®.

The activity of these solutions, alone or in combination, was more particularly tested in respect of *Staphylococcus aureus* ATCC 6538, *Escherichia coli* ATCC 11229 and *Candida albicans* ATCC 10231.

The tests were conducted in accordance with the procedure described in Chapter I/2.1 and 2.2 of Tichtlinien für die Prüfung und Bewertung chemischer Desinfektionsverfahren der DGHM/Guidelines for Testing and Evaluating Chemical Disinfection Processes of DGHM as at 1.1, 1981.

Tables IX, X and XI respectively illustrate the bactericidal and fungicidal activity of a 0.1% aqueous solution of chlorohexidine digluconate, a 0.1% aqueous solution of Bardac22® and a mixture of equal parts of both compounds. The procedures of which these Tables illustrate the results comprise incubation of 72 hours at 37° C. and the use of the following inactivating substances as controls:

A: 3% Tween®80+0.3% lecithin+0.1% cysteine
B: 3% Tween®80+3% saponin+0.1% cysteine+0.1% histidine;
C: 3% Tween®80+0.3% lecithin+0.1% histidine+0.5% sodium thiosulphate.

In these Tables, the sign "+" indicates an increase and the sign "−" denotes the absence of growth.

The following Table IX which illustrates the bactericidal and fungicidal activity of a 0.1% aqueous solution of chlorohexidine digluconate (1% of the test solution corresponds to 0.001/digluconate), shows the inhibition of the growth of *S. aureus* and of *E. coli* by a 0.5% dilution of the chlorohexidine digluconate solution referred to, corresponding to a concentration of active substance of 0.0005%; *C. albicans* is inhibited by a 1% dilution of the said solution (0.001% chlorohexadine digluconate). In Table X, the didecyl dimethyl ammonium chloride shows an even more pronounced effect of inhibiting gram positive organisms *S aureus* and *C. albicans* with a 0.1% dilution-(0.0001% didecyl dimethyl ammonium chloride) and an inhibition of *E. coli* (a gram negative organism) with a 0.5% dilution (=0.0005% didecyl dimethyl ammonium chloride) Table X.

Table XI shows that the association of these two antiseptics makes it possible to inhibit the growth of the aforesaid micro-organisms at significantly greater dilutions (action in respect of *E coli* and *C. albicans* at concentrations of 0.00025% chlorohexidine digluconate and 0.00025% didecyl dimethyl ammonium chloride; action in respect of *S. aureus* for a concentration of 0.00005% for each of the two aforesaid antiseptics).

TABLE IX

Chlorohexidine Digluconate Alone
(1% solution → 0.001% digluconate)

| Conc. % | S. aureus ATCC 6538 | | | | E. coli ATCC 11229 | | | | Candida albicans ATCC 1031 | | | |
|---|---|---|---|---|---|---|---|---|---|---|---|---|
| (vol/vol.) | not | A | B | C | not | A | B | C | not | A | B | C |
| 1.0 | − | + | + | + | − | + | + | + | − | + | + | + |
| 0.5 | − | + | + | + | − | + | + | + | + | + | + | + |
| 0.1 | + | + | + | + | + | + | + | + | + | + | + | + |
| 0.05 | + | + | + | + | + | + | + | + | + | + | + | + |

TABLE IX-continued

Chlorohexidine Digluconate Alone
(1% solution → 0.001% digluconate)

| Conc. % | S. aureus ATCC 6538 | | | | E. coli ATCC 11229 | | | | Candida albicans ATCC 1031 | | | |
|---|---|---|---|---|---|---|---|---|---|---|---|---|
| (vol/vol.) | not | A | B | C | not | A | B | C | not | A | B | C |
| 0.025 | + | + | + | + | + | + | + | + | + | + | + | + |
| 0.0125 | + | + | + | + | + | + | + | + | + | + | + | + |
| 0.00625 | + | + | + | + | + | + | + | + | + | + | + | + |

TABLE X

Bardac22® Alone
(1% solution → 0.001% Bardac22®)

| Conc. % | S. aureus ATCC 6538 | | | | E. coli ATCC 11229 | | | | Candida albicans ATCC 1031 | | | |
|---|---|---|---|---|---|---|---|---|---|---|---|---|
| (vol/vol.) | not | A | B | C | not | A | B | C | not | A | B | C |
| 1.0 | − | + | + | + | − | + | + | + | − | + | + | + |
| 0.5 | − | + | + | + | − | + | + | + | − | + | + | + |
| 0.1 | − | + | + | + | + | + | + | + | − | + | + | + |
| 0.05 | + | + | + | + | + | + | + | + | + | + | + | + |
| 0.025 | + | + | + | + | + | + | + | + | + | + | + | + |
| 0.0125 | + | + | + | + | + | + | + | + | + | + | + | + |
| 0.00625 | + | + | + | + | + | + | + | + | + | + | + | + |

TABLE XI

Composition according to the invention
(2% solution → 0.001% Bardac® and 0.001% CHG)

| Conc. % | S. aureus ATCC 6538 | | | | E. coli ATCC 11229 | | | | Candida albicans ATCC 1031 | | | |
|---|---|---|---|---|---|---|---|---|---|---|---|---|
| (vol/vol.) | not | A | B | C | not | A | B | C | not | A | B | C |
| 2.0 | − | + | + | + | − | + | + | + | − | + | + | + |
| 1.0 | − | + | + | + | − | + | + | + | − | + | + | + |
| 0.5 | − | + | + | + | − | + | + | + | − | + | + | + |
| 0.1 | − | + | + | + | + | + | + | + | + | + | + | + |
| 0.05 | + | + | + | + | + | + | + | + | + | + | + | + |
| 0.025 | + | + | + | + | + | + | + | + | + | + | + | + |
| 0.0125 | + | + | + | + | + | + | + | + | + | + | + | + |
| 0.00625 | + | + | + | + | + | + | + | + | + | + | + | + |

The tests, the results of which are illustrated in Tables XII, XIII and XIV, were conducted at reaction temperature of 22° C. with an incubation of the sub-cultures 72 hours at 37° C. with, as inactivating substances: 3% Tween® 80+3% saponin+0.1% cysteine+0.1% histidine; these Tables respectively illustrate the bactericidal and fungicidal activity of a 0.1% aqueous solution of chlorohexidine digluconate, of a 0.1% aqueous solution of Bardac® and a mixture of equal parts of the two compounds and show the action of the aforesaid antiseptics as a function of the contact time and cause the appearance of the same synergy of action of the association as above, in so far as the association of the two compounds makes it possible significantly to reduce their concentration in order to obtain the same effect.

TABLE XII

(CHG by itself)

| | Test Strain | | | | | | | | | | | | | | | | | |
|---|---|---|---|---|---|---|---|---|---|---|---|---|---|---|---|---|---|---|
| | S. aureus ATCC 6538 organisms/ml $8 \times 10^8$ | | | | | | E. coli ATCC 11229 organisms/ml $2 \times 10^9$ | | | | | | C. albicans ATCC 1031 organisms/ml $8 \times 10^7$ | | | | | |
| Conc. % | Disinfection time (minutes) | | | | | | | | | | | | | | | | | |
| (vol/vol.) | 1 | 3 | 5 | 15 | 30 | 60 | 1 | 3 | 5 | 15 | 30 | 60 | 1 | 3 | 5 | 15 | 30 | 60 |
| 25   | + | + | + | + | − | − | + | + | + | − | − | − | + | + | + | − | − | − |
| 10   | + | + | + | + | + | − | + | + | + | − | − | − | + | + | + | + | − | − |
| 5    | + | + | + | + | + | + | + | + | + | + | − | − | + | + | + | + | − | − |
| 1    | + | + | + | + | + | + | + | + | + | + | + | + | + | + | + | + | + | − |
| 0.5  | + | + | + | + | + | + | + | + | + | + | + | + | + | + | + | + | + | + |
| 0.1  | + | + | + | + | + | + | + | + | + | + | + | + | + | + | + | + | + | + |
| 0.05 | + | + | + | + | + | + | + | + | + | + | + | + | + | + | + | + | + | + |

TABLE XIII

(Bardac® by itself)

| | Test Strain | | | | | | | | | | | | | | | | | |
|---|---|---|---|---|---|---|---|---|---|---|---|---|---|---|---|---|---|---|
| | S. aureus ATCC 6538 organisms/ml $8 \times 10^8$ | | | | | | E. coli ATCC 11229 organisms/ml $2 \times 10^9$ | | | | | | C. albicans ATCC 1031 organisms/ml $8 \times 10^7$ | | | | | |
| Conc. % | Disinfection time (minutes) | | | | | | | | | | | | | | | | | |
| (vol/vol.) | 1 | 3 | 5 | 15 | 30 | 60 | 1 | 3 | 5 | 15 | 30 | 60 | 1 | 3 | 5 | 15 | 30 | 60 |
| 25   | + | − | − | − | − | − | − | − | − | − | − | − | − | − | − | − | − | − |
| 10   | + | − | − | − | − | − | + | + | − | − | − | − | − | − | − | − | − | − |
| 5    | + | + | + | − | − | − | + | + | + | − | − | − | + | + | − | − | − | − |
| 1    | + | + | + | + | − | − | + | + | + | + | + | + | + | + | + | + | + | + |
| 0.5  | + | + | + | + | + | + | + | + | + | + | + | + | + | + | + | + | + | + |
| 0.1  | + | + | + | + | + | + | + | + | + | + | + | + | + | + | + | + | + | + |
| 0.05 | + | + | + | + | + | + | + | + | + | + | + | + | + | + | + | + | + | + |

TABLE XIV

(Composition according to the Invention)

| | Test Strain | | | | | | | | | | | | | | | | | |
|---|---|---|---|---|---|---|---|---|---|---|---|---|---|---|---|---|---|---|
| | S. aureus ATCC 6538 organisms/ml $8 \times 10^8$ | | | | | | E. coli ATCC 11229 organisms/ml $2 \times 10^9$ | | | | | | C. albicans ATCC 1031 organisms/ml $8 \times 10^7$ | | | | | |
| Conc. % | Disinfection time (minutes) | | | | | | | | | | | | | | | | | |
| (vol/vol.) | 1 | 3 | 5 | 15 | 30 | 60 | 1 | 3 | 5 | 15 | 30 | 60 | 1 | 3 | 5 | 15 | 30 | 60 |
| 25   | + | − | − | − | − | − | − | − | − | − | − | − | + | − | − | − | − | − |
| 10   | + | + | + | − | − | − | − | − | − | − | − | − | + | − | − | − | − | − |
| 5    | + | + | + | + | − | − | + | − | − | − | − | − | + | + | + | − | − | − |
| 1    | + | + | + | + | + | + | + | + | + | − | − | − | + | + | + | + | + | + |
| 0.5  | + | + | + | + | + | + | + | + | + | + | + | + | + | + | + | + | + | + |
| 0.1  | + | + | + | + | + | + | + | + | + | + | + | + | + | + | + | + | + | + |
| 0.05 | + | + | + | + | + | + | + | + | + | + | + | + | + | + | + | + | + | + |

EXAMPLE 5

Spermicidal Action

Procedure

The various samples of sperm (one drop of sperm per sample) are obtained from healthy volunteers.

Measurement of Vitality

One drop of sperm is treated by eosine-nigrosine. A smear is then prepared and 100 spermatozoids examined with a microscope. The dead cells are coloured red, either totally or partially. The living cells are colourless.

Substances Studied

The substances studied were Bardac® and chlorohexidine digluconate, tested alone and in association in accordance with the invention. The various stages of the procedure are set out in Tables XV to XVII.

The maximum contact time of the various substances and of the sperm was confined to 3 minutes in order to guarantee the effectiveness of the method under the conditions of use. The concentration of the active solutions in the sperm was limited to 10% in order to reduce the risks of toxicity of the products in respect of the mucosa.

TABLE XV

| Bardac | | Contact time of substances and sperm | | | |
|---|---|---|---|---|---|
| | Concentrations of solutions in terms | 1 min | | 3 min | |
| | | Concentrations of the solutions in the sperm | | | |
| Control at T0 | active substances | 5% | 10% | 5% | 10% |
| 82.8 ± 7.1 | 0.4% | 10.7 ± 7.6 | 5 ± 6.4 | 0.8 ± 1.2 | 0.8 ± 1 |
| 81.4 ± 5.9 | 0.6% | 10.5 ± 9.7 | 9.2 ± 12.9 | 2.2 ± 4.5 | 0.4 ± 0.9 |
| 81.4 ± 5.9 | 0.8% | 9.7 ± 10.2 | 1.8 ± 2.5 | 0 | 0 |
| 79.7 ± 5.3 | 1% | 0 | 0 | 0 | 0 |

TABLE XVI

| Chlorohexidine Digluconate | | | | | |
|---|---|---|---|---|---|
| | Concentrations of solutions in terms active substances | Contact time of substances and sperm | | | |
| Control at T0 | | 1 min | | 3 min | |
| | | Concentrations of the solutions in the sperm | | | |
| | | 5% | 10% | 5% | 10% |
| 98 ± 6.2% | 0.5% | 77 ± 10.8 | 77.2 ± 5.6 | 78 ± 5.7 | 75.5 ± 4.8 |

TABLE XVII

| Bardac + Chlorohexidine digluconate | Contact time of substances and sperm | | | |
|---|---|---|---|---|
| Concentrations of solutions in terms | 1 min | | 3 min | |
| | Concentrations of the solutions in the sperm | | | |
| Control at T0 active substances | 5% | 10% | 5% | 10% |
| 88.4 ± 5.4% B 0.4% + DC 0.5% | 15.6 ± 13.2 | 5.1 ± 8 | 8.6 ± 10.8 | 2.4 ± 4.1 |
| B 0.4% + DC 0.8% | 21.3 ± 14 | 6.7 ± 3 | 18.3 ± 13.3 | 6.3 ± 7.8 |
| B 0.4% + DC 1% | 19 ± 11.1 | 10 ± 8.7 | 16 ± 9.8 | 9.3 ± 11.9 |
| B 0.6% + DC 0.5% | 6.3 ± 11 | 4 ± 6.9 | 1.3 ± 2.3 | 1 ± 1.7 |
| B 0.8% + DC 0.5% | 3.7 ± 6.3 | 0 | 2 ± 3.5 | 0 |

EXAMPLE 6

Study of the Mixture of Bardac22® and Chlorohexidine Digluconate in Aqueous Solution All the mixtures were prepared in weight/weight percentages in plastic phials kept away from the light and at room temperature (20° C.±1° C.).

Daily observations of these phials made it possible or not to detect the presence of a white precipitate. This (when it forms) is found on the residue of the majority phial but also on the walls wetted by the liquid.

Study of 50/50 Solutions of Bardac22® Chlorohexidine at Various Concentrations

The study was conducted in a first stage on aqueous solutions at different concentrations of active principles but for a mixture of the two active principles (Bardac® and chlorohexidine digluconate) in equal proportions (50/50):

30% solution of active principles—precipitated at 24 hours

20% solution of active principles—precipitated at 24 hours

10% solution of active principles—precipitated at 24 hours

5% solution of active principles—precipitated at 24 hours

1% solution of active principles—precipitated at 24 hours

Study of 10 and 20% Solutions of Bardac® and Chlorohexidine in Different Proportions In a second stage, the concentrations of active principles were fixed at 10% and 20% but the proportions of the two active principles were varied.

TABLE XVIII

Recapitulative Table of the 10% Solutions Of Active Principles

| Ratio of chlorohexidine digluconate/ Bardac ® | chlorohexidine digluconate (%) | Bardac ® (%) | Remarks |
|---|---|---|---|
| 0.5/99.5 | 0.05 | 9.95 | no precipitation |
| 1/99 | 0.1 | 9.9 | no precipitation |
| 2/98 | 0.2 | 9.8 | no precipitation |
| 4/96 | 0.4 | 9.6 | no precipitation |
| 8/92 | 0.8 | 9.2 | no precipitation |
| 16/84 | 1.6 | 8.4 | no precipitation |
| 25/75 | 2.5 | 7.5 | precipitation at 2 months |
| 35/65 | 3.5 | 6.5 | precipitation at 9 days |
| 40/60 | 4.0 | 6.4 | precipitation at 6 days |
| 50/50 | 5.0 | 5.0 | precipitation at 24 hours |

TABLE XIX

Recapitulative Table of the 20% Solutions of Active Principles

| Ratio of chlorohexidine digluconate/ Bardac ® | chlorohexidine digluconate (%) | Bardac ® (%) | Remarks |
|---|---|---|---|
| 0.5/99.5 | 0.1 | 19.9 | no precipitation |
| 1/99 | 0.2 | 19.8 | no precipitation |
| 2/98 | 0.4 | 19.6 | no precipitation |
| 4/96 | 0.8 | 19.2 | no precipitation |
| 8/92 | 1.6 | 18.4 | no precipitation |
| 3.2 | 16.8 | 8.4 | no precipitation |
| 25/75 | 5.0 | 15.0 | precipitation at 2 months |
| 35/65 | 7.0 | 13.0 | precipitation at 9 days |
| 40/60 | 8.0 | 12.0 | precipitation at 6 days |
| 50/50 | 10.0 | 10.0 | precipitation at 24 hours |

EXAMPLE 7

Study of the Mixture of the Bardac 22® Chlorohexidine Digluconate in Alcohol Solution The dissolutions in the proportions indicated for water are identical when the two products are in solution in glycerol.

EXAMPLE 8

Study of the Disinfectant Capacity in Respect of Bacteria and Fungi of Microcapsules Containing a Composition According to the Invention and Included in a Polyvinyl Cloth After the said Tissue has been Punctured by a Needle.

Material and Method

Two samples of microcapsules included in polyvinyl or latex cloths comprise:
- sample 1: microcapsules containing a composition according to the invention, included in PVDC. The thickness of the cloth covering the microcapsules is around 500 μm and the total thickness of the cloth is around 1300 μm and the quantity of disinfectant available after the cloth has been torn by a needle (0.5×16 mm) is approx. 1.5 μg;
- sample 2: microcapsules containing a composition according to the invention of the even type I, included in the EVA. The thickness of the cloth covering the micro-capsules is about 500 μm and the quantity of disinfectant available after the cloth has been torn by a needle (0.5×16 mm) is approx. 0.4 μg.

The microbiological samples for carrying out the test are prepared using the following micro-organisms: *Escherichia coli* ATCC 11229, *Staphylococcus aureus* ATCC 6538 and *Candida albicans* ATCC 10231.

The strains are cultivated in a CSL medium (Merck) for 24 hours at 37° C., then dilutions comprised between $10^{-3}$ and $10^{-6}$ are prepared in a 0.9% sodium chloride solution.

One millilitre of each of the various cultures obtained (diluted and not diluted) is added to 9 ml of a pool of inactivated human serum. The number of micro-organisms per ml of the test solution is mentioned in the following Table XX.

Three types of needle were used: 0.7×30 mm (22 G×¼", Terumo), 0.5×16 mm (25 G×⅝", Terumo), 0.3×13 nun (30 G×½", Microlance, Becton Dickinson).

These needles are mounted on 1 ml syringes, steeped in a microbial solution as described above (at least 1 cm of the needle must be steeped in the solution) and 0.1 ml of solution is aspirated. It then pierces the above-described cloths, placed in Petri dishes covered with casoagar (Merck, medium supplemented by 3% of Tween® 80 and 0.3% lecithin) with the said needles.

The sites where the agar is inoculated by the needle are marked, then the culture media are incubated for 72 hours at 37° C. prior to reading of the results.

Results

Table XX shows the number of positive cultures obtained after perforation (5 perforations per test) with a 0.3×13 mm (30 G×½", Microlance, Becton-Dickinson) needle, and culture of the perforated cloth on a casoagar medium (Merck) supplemented as stipulated above.

TABLE XX

Number of positive cultures obtained after perforation

| Microbial solution | Sample 1 | | Sample 2 | |
|---|---|---|---|---|
| | Micro-capsules | Control | Micro-capsules | Control |
| *E. coli* | | | | |
| $3 \times 10^8$/ml | + - - - - | + + + + - | + + + - - | + + + + + |
| $2 \times 10^2$/ml | - - - - - | - - - - - | - - - - - | - - - - - |
| $10^2$/ml | - - - - - | - - - - - | - - - - - | - - - - - |
| *S. aureus* | | | | |
| $2 \times 10^8$/ml | + + + - - | + + + + + | + + + + + | + + + + + |
| $2 \times 10^5$/ml | - - - - - | - - - - - | - - - - - | - - - - - |
| $10^2$/ml | - - - - - | - - - - - | - - - - - | - - - - - |
| *C. albicans* | | | | |
| $3 \times 10^7$/ml | - - - - - | + - - - - | + + - - - | + + - - - |
| $3 \times 10^5$/ml | - - - - - | - - - - - | - - - - - | - - - - - |
| $10^2$/ml | - - - - - | - - - - - | - - - - - | - - - - - |

+ growth of micro-organisms
− absence of growth

These results show in particular that small concentrations of bacteria or fungi ($10^2$/ml) are absorbed or eliminated mechanically by the polyvinyl cloths; a concentration of 105 organisms per millilitre may be regarded as the limit which produces no growth when the smallest needles are used (9.3×13 mm, Table X; on the other hand, results of the same order are obtained with the needles measuring 0.7×30 mm and 0.5×16 mm respectively. Growth is only obtained for high concentrations of bacteria ($10^8$/ml) or fungi ($10^7$/ml), upon perforation of the control cloths only (sample 1).

These results likewise show that the microcapsules of sample 1 (PVDC) are more effective than the microcapsules of sample 2 (EVA).

Conclusion

The tests conducted with sample 1 show these virtually instantaneous disinfectant effects of the compositions according to the invention incorporated into microcapsules under conditions approximating those encountered at a hospital.

EXAMPLE 9

Effects of Compounds on the Hemolysis of Erythrocytes

The effect of the compounds on the in-vitro hemolysis of erythrocytes in heparinized whole blood is monitored by a spectrophotometric method.

Various formulations and concentrations of the test compound are added to heparinized bovine blood and mixed gently in a 1.5 ml microcentrifuge tube. The sample is allowed to incubate for 1 hour at 37° C. At the end of incubation, the samples are removed from the incubator and centrifuged at 2000 rpm for 5 minutes. A 200 µl aliquot of the supernatant is removed from each sample into a 96 well microtiter plate and read at 413 nm. The absorbance of the test sample is compared to the control sample containing phosphate buffered saline, pH 7.2. Absorbance reading of the test samples that are higher than the control sample are deemed to be hemolytic.

Table XXI summarizes the concentration and the components of the test compounds that are non-hemolytic under the test conditions.

TABLE XXI

Non-hemolytic Test Compounds

| Test Compound Components | Concentration at which hemolysis is not observed |
|---|---|
| Bardac 22 ® | 0.0125% |
| Chlorohexidine Gluconate | 0.0125% |
| Bardac 22 ® | 0.0125% |
| Chlorohexidine Gluconate | 0.0125% |
| Decamethonium Iodide | 0.0125% |
| Bardac 22 ® | 0.001% |
| Chlorohexidine Gluconate | 0.001% |
| Tergitol NP-9 | 0.001% |
| Bardac 22 ® | 0.0125% |
| Chlorohexidine Gluconate | 0.0125% |
| Hexamethonium Bromide | 0.0125% |
| Bardac 22 ® | 0.0005% |
| Chlorohexidine Gluconate | 0.0005% |
| Tri-n-Butyl Phosphate | 0.0005% |

Although the present invention has been described in terms of a particular preferred embodiments, it is not limited to those embodiments. Alternative embodiments, examples, and modifications which would still be encompassed by the invention may be made by those skilled in the art, particularly in light of the foregoing teachings.

What is claimed is:

1. A non-hemolytic method for inhibiting in vitro or ex vivo a pathogen in a blood sample, comprising treating said blood sample with an effective inhibiting amount of a composition which consists of didecyl dimethyl ammonium chloride digluconate and chlorohexidine digluconate, each of which is present at a concentration of 0.002%, in combination with a pharmaceutically acceptable carrier, wherein red blood cells remain intact in said blood sample.

2. A non-hemolytic method for in vitro or ex vivo disinfecting a red blood cell sample, said method comprising the steps of:
   a. contacting said red blood cell sample with a disinfecting composition for a period of time sufficient to inactivate pathogen present in said red blood cell sample, wherein said disinfecting composition consists of a composition which comprises didecyl dimethyl ammonium chloride and chlorohexidine digluconate, each of which is present at a concentration of 0.002%, in association with a solution of an isotonic effective concentration of solute, whereby said disinfecting composition is substantially isotonic with red blood cells; and
   b. isolating said red blood cells from said disinfecting composition, wherein the red blood cells remain intact.

3. The method of claim 2, further comprising removing the composition after inactivating the pathogen.

* * * * *